United States Patent [19]

Hodgson et al.

[11] Patent Number: 5,891,667
[45] Date of Patent: Apr. 6, 1999

[54] SPOIIIE POLYNUCLEOTIDES

[75] Inventors: John Edward Hodgson, Malvern; Alison Frances Chalker, Collegeville, both of Pa.

[73] Assignee: SmithKline Beecham, p.l.c., United Kingdom

[21] Appl. No.: 785,431

[22] Filed: Jan. 17, 1997

[30] Foreign Application Priority Data

Jan. 17, 1996 [GB] United Kingdom .................. 9600955

[51] Int. Cl.$^6$ ........................... C12N 15/00; C12N 15/09; C07K 14/31; A61K 39/085
[52] U.S. Cl. ................. 435/69.1; 435/320.1; 435/252.3; 435/240.2; 435/7.33; 536/23.1; 536/24.3; 536/24.32; 530/350; 530/825; 935/1; 935/6; 935/8; 935/11; 935/19; 935/52; 424/243.1
[58] Field of Search .................................. 536/23.1, 24.3, 536/24.32; 435/69.1, 320.1, 252.3, 240.2, 7.33; 530/350, 825; 935/1, 6, 8, 11, 19, 52; 424/243.1

[56] References Cited

U.S. PATENT DOCUMENTS 4,879,213  11/1989  Fox et al. .
5,151,350   9/1992  Colbert et al. .

OTHER PUBLICATIONS

Lehmeyer Biochemistry, 2nd ed., Worth Publishers, Inc., N.Y.N.Y. (1975) & P. 63.
Burgess et al., J. Cell Brol. 1990 vol. 111, 2129–2138.
Lazar et al Mol. Cell. Brol. 1988. vol. 8, No. 3, 1247–1252.
Fleischmann et al. (Science 1995), vol. 269, 496–512.
Wu, et al., "*Bacillus subtillis* SpoIIIE Protein Required for DNA Segregation During Asymmetric Cell Division", *Science*, 264, pp. 572–575 (1994).
Begg, et al., "A New *Escherichia coli* Cell Division Gene, ftsK", Journal of Bacteriology, 177(21), pp. 6211–6222 (1995).
Wu, et al., "A conjugation–like mechanism for prespore chromosome partitioning during sporulation in *Bacillus subtilis*", *Genes & Development*, 9, pp. 1316–1326 (1995).
Ceglowski, et al., "Gene organization of the Streptococcus pyogenes plasmid pDB 101:sequence analysis of the orfn–copS region", *Gene*, 145, pp. 33–39 (1994).
Oswald, et al., "A Sporulation Gene in Coxiella–burnetii", *J. Vet. Med.*, 40, pp. 366–370 (1993).
Butler, et al., "Nucleotide Sequence of the Sporulation Operon, *spoIIIE*, of *Bacillus subtilis*", Journal of General Microbiology, 133, pp. 2359–2370 (1987).
Fleischmann, et al., "Whole–Genome Random Sequencing and Assembly of *Haemophilus influenzae*Rd", *Science*, 269, pp. 469–512, (1995).

*Primary Examiner*—Paula K. Hutzell
*Assistant Examiner*—Khalid Masood
*Attorney, Agent, or Firm*—Edward R. Gimmi; William T. King; Arthur E. Jackson

[57] ABSTRACT

The invention provides spoIIIE polypeptides and DNA (RNA) encoding spIIIE polypetides and methods for producing such polypeptides by recombinant techniques. Also provided are methods for utilizing spoIIIE polypeptide for the protection against infection, particularly bacterial infections.

9 Claims, 4 Drawing Sheets

FIGURE 1. spoIIIE cloned DNA sequence [SEQ ID NO:1 and SEQ ID NO:3]

```
  1  ttggctcaag caaaaaagaa atcgacagct aagaaaaaaa cagCATCAAA
 51  AAAAGAACA  AATTCAAGGA AAAAGAAGAA TGATAATCCG ATACGTTATG
101  TCATAGCTAT TTTAGTAGTT GTATTAATCG TGTTGGGTGT TTTCCAATTA
151  GGAATAATCG GTCGTCTAAT TGACAGCTTC TTTAATTATT TATTTGGGTA
201  CAGTAGATAT TTAACATATA TTTTAGTACT CTTAGCAACT GGTTTTATTA
251  CATACTCTAA ACGTATTCCT AAAACTAGAC GAACGGCTGG TTCGATTGTA
301  TTGCAAATTG CATTGCTATT TGTATCACAG TTAGTTTTTC ATTtaatag
351  tGGTATCAAA GCTGAAAGAG AACCTGTACT TTCTTATGTA TATCAGTCAT
401  ACCAACACAG TCATTTTCCA AATTTTGGTG GCGGTGTATT AGTTTTTAT
451  TTATTAGAGT TAAGCGTaCC TTTAATTTCA TTATTGGTG TATGTATTAT
501  TACTATTTTA TTATTATGCT CAAGTGTTAT TTTATTAACA AACCATCAAC
551  ATCGTGATGT TGCAAAAGTT GCACTGGAAA ATATAAAAGC TTGGTTTGGT
601  TCATTTAATG AAAAAAATGT GGAAAGAAAC CAAGAAAAAC AATTGAAGCG
651  .TGAAGAAAA  GCCGAGACTT AAGAAGAACA AAAGGCACGT CAAAATGAAC
701  AGCCACAAAT AAAAGATGTG AGTGATTTTA CGGAAGTGCC TCAAGAAAGA
751  GATATTCCAA TTTATGGGCA TACTGAAAAT GAAAGTAAAA GCCAGTGTCA
801  ACCAAGTCGA AAAAAACGAG TGTTTGATGC AGAGAATAGT TCGAATAACA
```

Figure 1A

```
 851  TCGTAAATCA TCAAGCAGAT CAGCAAGAGC AATTAACAGA ACAAACTCAT
 901  AACAGTGTTG AAAGTGAAAA CACTATTGAA GAAGCTGGTG AAGTTACGAA
 951  TGTATCGTAT GTTGTTCCAC CGTTAACTTT ACTTAATCAA CCTGCAAAAC
1001  AAAAAGCAAC ATCTAAAGCT GAAGTACAAC GTAAAGGACA AGTACTAGAG
1051  AATACATTAA AAGATTTTGG GGTAAATGCA AAAGTGACAC AAATTAAAAT
1101  TGGTCCTGCA GTAACTCAAT ATGAAATTCA ACCAGCTCAA GGGGTTAAAG
1151  TGAGTAAAAT TGTAAACTTG CATAATGATA TTGCATTAGC TTTAGCAGCA
1201  AAAGATGTTA GAATCGAAGC ACCAATACCT GGTCGCTCTG CAGTAGGTAT
1251  TGAAGTGCCA AATGAGAAAA TTTCATTAGT TTCACTAAAA GAAGTTTTAG
1301  ATGAAAAATT CCCGTCTAAT AATAAACTAG AAGTTGGATT AGGAAGAGAT
1351  ATATCAGGTG ATCCAATTAC TGTTCCACTA AATGAAATGC CACACTTATT
1401  GGTGGCAGGA TCGACGGGTA GTGGTAAATC TGTTTGTATA AATGGTATTA
1451  TTACAAGTAT TTTATTAAAT GCTAAGCCGC ATGAAGTTAA ACTTATGTTA
1501  ATCgATCCGA AAATGGTTGA ACTAAATGTT TATAACGgaa ttcCACATTT
1551  ATTAATTCCG GTTGTTACAA ATCCTCaTAA AGCTGCTCAA GCTTTAGAAA
1601  AAATTGTAGC TGAGATGGAA AGACGTTATG ATTATTCCA ACATTCATCA
1651  ACTAGAAATA TTAAAGGTTA TAACGAATTA ATCCGTAAGC AAAATCAAGA
```

Figure 1B

```
1701 ATTAGATGAG AAGCAACCAG AATTACCTTA TATCGTTGTT ATTGTAGATG
1751 AGCTTGCAGA TTTAATGATG GTAGCTGGTA AAGAAGTTGA AAATGCGATT
1801 CAACGTATCA CACAAATGGC ACGTGCAGCA GGTATACATT TGATTGTAGC
1851 AACACAAAGA CCTTCTGTGG ATGTAATTAC AGGTATCATT AAAAATAACA
1901 TTCCATCTAG AATTGCTTTT GCTGTGAGTT CTCAAACAGA TTCAAGAACT
1951 ATTATTGGTA CTGGCGGCGC AGAAAAGTTA CTTGGTAAAG GTGACATGTT
2001 ATACGTTGGA AATGGTGATT CATCACAAAC ACGTATTCAA GGGGCGTTTT
2051 TAAGTGACCA AGAGGTGCAA GATGTTGTAA ATTATGTAGT AGAACAACAA
2101 CAGGCAAATT ATGTAAAAGA AATGGAACCA GATGCACCAG TGGATAAATC
2151 GGAAATGAAA AGTGAAGATG CTTTATATGA TGAAGCGTAT TTGTTTGTTG
2201 TTGAACAACA AAAGGCAAGT ACATCATTGT TACAACGCCA ATTAGAATT
2251 GGTTATAATA GAGCATCTAG GTTGATGGAT GATTAGAAAC GCAATCAGT
2301 AATCGGTCCA CAAAAAGGAA GCAAGCCTAG ACAAGTTTTA ATAGATCTTA
2351 ATAATGACGA GGTGTAA
```

FIGURE 2. spoIIIE deduced amino acid sequence [SEQ ID NO:2 and SEQ ID NO:4]

```
  1  LAQAKKKSTA KKKTASKKRT NSRKKKNDNP IRYVIAILVV VLMVLGVFQL
 51  GIIGRLIDSF FNYLFGYSRY LTYILVLLAT GFITYSKRIP KTRRTAGSIV
101  LQIALLFVSQ LVFHFNSGIK AEREPVLSYV YQSYQHSHFP NFGGGVLGFY
151  LLELSVPLIS LFGVCIITIL LLCSSVILLT NHQHRDVAKV ALENIKAWFG
201  SFNEKMSERN QEKQLKREEK ARLKEEQKAR QNEQPQIKDV SDFTEVPQER
251  DIPIYGHTEN ESKSQCQPSR KKRVFDAENS SNNIVNHQAD QQEQLTEQTH
301  NSVESENTIE EAGEVTNVSY VVPPLTLLNQ PAKQKATSKA EVQRKGQVLE
351  NTLKDFGVNA KVTQIKIGPA VTQYEIQPAQ GVKVSKIVNL HNDIALALAA
401  KDVRIEAPIP GRSAVGIEVP NEKISLVSLK EVLDEKFPSN NKLEVGLGRD
451  ISGDPITVPL NEMPHLLVAG STGSGKSVCI NGIITSILLN AKPHEVKLML
501  IDPKMVELNV YNGIPHLLIP VVTNPHKAAQ ALEKIVAEME RRYDLFQHSS
551  TRNIKGYNEL IRKQNQELDE KQPELPYIVV IVDELADLMM VAGKEVENAI
601  QRITQMARAA GIHLIVATQR PSVDVITGII KNNIPSRIAF AVSSQTDSRT
651  IIGTGGAEKL LGKGDMLYVG NGDSSQTRIQ GAFLSDQEVQ DVVNYVVEQQ
701  QANYVKEMEP DAPVDKSEMK SEDALYDEAY LFVVEQQKAS TSLLQRQFRI
751  GYNRASRLMD DLERNQVIGP QKGSKPRQVL IDLNNDEV
```

SPOIIIE POLYNUCLEOTIDES

This application claims foreign priority of U.K. application 9600955.0 filed Jan. 17,1996.

FIELD OF THE INVENTION

This invention relates to newly identified polynucleotides and polypeptides, and their production and uses, as well as their variants, agonists and antagonists, and their uses. In particular, in these and in other regards, the invention relates to polynucleotides and polypeptides of the spo family, hereinafter referred to as "spoIIIE".

BACKGROUND OF THE INVENTION

It is particularly preferred to employ Staphylococcal genes and gene products as targets for the development of antibiotics. The Staphylococci make up a medically important genera of microbes. They are known to produce two types of disease, invasive and toxigenic. Invasive infections are characterized generally by abscess formation effecting both skin surfaces and deep tissues. *S. aureus* is the second leading cause of bacteremia in cancer patients. Osteomyelitis, septic arthritis, septic thrombophlebitis and acute bacterial endocarditis are also relatively common. There are at least three clinical conditions resulting from the toxigenic properties of Staphylococci. The manifestation of these diseases result from the actions of exotoxins as opposed to tissue invasion and bacteremia. These conditions include: Staphylococcal food poisoning, scalded skin syndrome and toxic shock syndrome.

SpoIIIE is a membrane bound protein involved in chromosome partitioning during sporulation and vegetative replication in a wide variety of bacteria. The spoIIIE gene was initially characterised in *Bacillus subtilis* (Butler P. D. and Mandelstam J. (1987) Journal of General Microbiology 133:2359–2370). SpoIIIE protein has an ATP binding site and is membrane-bound, and appears to form a pore in the nascent spore septum, through which the prespore chromosome is driven in a conjugation-like mechanism (Wu L. J., Lewis P. J., Allmansberger R., Hauser P. M. and Errington J. (1995) Genes and Development 9:1316–1326). spoIIIE mutants cannot sporulate as they are unable to partition the prespore chromosome into the polar prespore compartment. Instead a specific chromosomal segment comprising approximately 30% of the chromosome enters the prespore, while the rest remains in the mother cell, trapped by the septum (Wu L. J. and Errington J. (1994) Science 264:572–575). In wild-type cells SpoIIIE is membrane-bound, and appears to form a pore in the nascent spore septum, through which the prespore chromosome is driven in a conjugation-like mechanism (Wu L. J., Lewis P. J., Allmansberger R., Hauser P. M. and Errington J. (1995) Genes and Development 9:1316–1326).

It has been shown that SpoIIIE is also required for correct partitioning of the *B. subtilis* chromosome during vegetative cell division. spoIIIE-Mutants in which replication has been artificially delayed are unable to separate the replicated chromosomes before septum formation, resulting in a trapped nucleoid similar to that formed at the start of sporulation (Sharpe M. E. and Errington J. (1995) Proceedings of the Natural Academy of Sciences USA 92:8630–8634).

SpoIIIE has been shown to be essential in *Escherichia coli* (Begg K. J., Dewar, S. J. and Donachie W. D. (1995) Journal of Bacteriology 177:6211–6222). Highly conserved SpoIIIE homologues are found in diverse members of the eubacteria such as *Campylobacter jejuni* (Miller, S., Pesci E. C. and Pickett C. L. (1994) Gene 146:31–38), *Coxiella burnetii* (Oswald W. and Thiele D. (1993) Journal of Veterinary Medecine B40:366–370), *Eshcerichia coli* (Begg 1995 above) and *Haemophilus influenzae* (Fleischmann, R. D., Adams, M. D., White, O., Clayton, R. A., Kirkness, E. F., Kerlavage, A. R., Bult, C. J., Tomb, J.-F., Dougherty, B. A., Merrick, J. M., McKenney, K., Sutton, G., FitzHugh, W., Fields, C. A., Gocayne, J. D., Scott, J. D., Shirley, R., Liu, L.-I., Glodek, A., Kelley, J. M., Weidman, J. F., Phillips, C. A., Spriggs, T., Hedblom, E., Cotton, M. D., Utterback, T. R., Hanna, M. C., Nguyen, D. T., Saudek, D. M., Brandon, R. C., Fine, L. D., Fritchman, J. L., Fuhrmann, J. L., Geoghagen, N. S. M., Gnehm, C. L., McDonald, L. A., Small, K. V., Fraser, C. M., Smith, H. O. and Venter, J. C. (1995) Science 269:496–512). All of these proteins are 36–55% identical at the amino acid level overall. Their N-terminal 200 amino acids are hydrophobic and not conserved, so if the C-terminal 500 or so amino acids are considered alone the level of conservation rises to 42–67% identical amino acids. This high level of identity among diverse eubacteria strongly suggests commonality of function.

Inhibitors of SpoIIIE proteins would prevent the bacterium from establishing and maintaining infection of the host by preventing it from correctly partitioning the chromosome in the manner described above and thus arresting cell division and growth, rendering the bacterium susceptible to host defences and leading ultimately to cell death and thereby have utility in anti-bacterial therapy.

Clearly, there is a need for factors that may be used to screen compounds for antibiotic activity and which factors may also be used to determine their roles in pathogenesis of infection, dysfunction and disease. There is also a a need for identification and characterization of such factors and their antagonists and agonists which can play a role in preventing, ameliorating or correcting infections, dysfinctions or diseases.

The polypeptides of the invention have amino acid sequence homology to a known *B. subtilis* spoIIE protein.

SUMMARY OF THE INVENTION

It is an object of the invention to provide polypeptides that have been identified as novel spoIIIE polypeptides by homology between the amino acid sequence set out in FIG. 2 and a known amino acid sequence or sequences of other proteins such as *B. subtilis* spoIIE protein.

It is a further object of the invention to provide polynucleotides that encode spoIIIE polypeptides, particularly polynucleotides that encode the polypeptide herein designated spoIIIE.

In a particularly preferred embodiment of this aspect of the invention the polynucleotide comprises a region encoding spoIIIE polypeptides comprising the sequence set out in FIG. 1 [SEQ ID NO:1 and SEQ ID NO:3], or a variant thereof.

In another particularly preferred embodiment of the invention there is a novel spoIIIE protein from *Staphylococcus aureus* comprising the amino acid sequence of FIG. 2 [SEQ ID NO:2 and SEQ ID NO:4], or a variant thereof.

In accordance with this aspect of the invention there is provided an isolated nucleic acid molecule encoding a mature polypeptide expressible by the *Staphylococcus aureus* WCUH 29 strain contained in NCIMB Deposit No. 40771.

In accordance with this aspect of the invention there are provided isolated nucleic acid molecules encoding spoIIIE, particularly *Staphylococcus aureus* spoIIIE, including mRNAs, cDNAs, genomic DNAs. Further embodiments of this aspect of the invention include biologically, diagnostically, prophylactically, clinically or therapeutically useful variants thereof, and compositions comprising the same.

In accordance with another aspect of the invention, there is provided the use of a polynucleotide of the invention for therapeutic or prophylactic purposes, in particular genetic immunization. Among the particularly preferred embodiments of this aspect of the invention are naturally occurring allelic variants of spoIIIE and polypeptides encoded thereby.

In accordance with this aspect of the invention there are provided novel polypeptides of *Staphylococcus aureus* referred to herein as spoIIIE as well as biologically, diagnostically, prophylactically, clinically or therapeutically useful variants thereof, and compositions comprising the same.

Among the particularly preferred embodiments of this aspect of the invention are variants of spoIIIE polypeptide encoded by naturally occurring alleles of the spoIIIE gene.

In a preferred embodiment of this aspect of the invention there are provided methods for producing the aforementioned spoIIIE polypeptides.

In accordance with yet another aspect of the invention, there are provided inhibitors to such polypeptides, useful as antibacterial agents, including, for example, antibodies.

In accordance with certain preferred embodiments of this aspect of the invention, there are provided products, compositions and methods for (i) assessing spoIIIE expression, (ii) treating disease, for example, disease, such as, infections of the upper respiratory tract (e.g. otitis media, bacterial tracheitis, acute epiglottitis, thyroiditis), lower respiratory (e.g. empyema, lung abscess),cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal and orbital cellulitis, darcryocystitis), kidney and urinary tract (e.g. epididymitis, intrarenal and perinephric abscess, toxic shock syndrome), skin (e.g. impetigo, folliculitis, cutaneous abscesses, cellulitis, wound infection, bacterial myositis) bone and joint (e.g. septic arthritis, osteomyelitis), (iii) assaying genetic variation, (iv) and administering a spoIIIE polypeptide or polynucleotide to an organism to raise an immunological response against a bacteria, especially a *Staphylococcus aureus* bacteria.

In accordance with certain preferred embodiments of this and other aspects of the invention there are provided polynucleotides that hybridize to spoIIIE polynucleotide sequences, particularly under stringent conditions.

In certain preferred embodiments of this aspect of the invention there are provided antibodies against spoIIIE polypeptides.

In accordance with another aspect of the invention, there are provided spoIIIE agonists and antagonists each of which are also preferably bacteriostatic or bacteriocidal.

In a further aspect of the invention there are provided compositions comprising a spoIIIE polynucleotide or a spoIIIE polypeptide for administration to a cell or to a multicellular organism.

Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIG. 1 shows the polynucleotide sequence of *Staphylococcus aureus* spoIIIE [SEQ ID NO:1 and SEQ ID NO:3]. The TTG start codon is shown in bold and underlined. The ATG start codon is shown italicized and underlined. The stop codon (UAA) is shown underlined.

FIG. 2 shows the amino acid sequence of *Staphylococcus aureus* spoIIIE [SEQ ID NO:2 and SEQ ID NO:4] deduced from the polynucleotide sequence of FIG. 1. Methionine number 43 is shown in bold.

GLOSSARY

The following definitions are provided to facilitate understanding of certain terms used frequently herein.

"Host cell" is a cell which has been transformed or transfected, or is capable of transformation or transfection by an exogenous polynucleotide sequence.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). While there exist a number of methods to measure identity and similarity between two sequences, both terms are well known to skilled artisans (*Sequence Analysis in Molecular Biology*, von Heinje, G., Academic Press, 1987; *Sequence Analysis Primer*, Gribskov, M. and Devereux, J., eds., M Stockton Press, New York, 1991; and Carillo, H., and Lipman, D., SIAM *J. Applied Math.*, 48:1073 (1988). Methods commonly employed to determine identity or similarity between sequences include, but are not limited to those disclosed in Carillo, H., and Lipman, D., SIAM *J. Applied Math.*, 48:1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, GCG program package (Devereux, J., et al., *Nucleic Acids Research* 12(1): 387 (1984)), BLASTP, BLASTN, and FASTA (Atschul, S. F. et al., *J. Molec. Biol.* 215: 403–410 (1990)). The BLAST X program is publicly available from NCBI and other sources (*BLAST Manual*, Altschul, S., et al., NCBI NLM NIH Bethesda, Md. 20894; Altschul, S., et al., *J. MoL Biol.* 215: 403–410 (1990)).

"Isolated" means altered "by the hand of man" from its natural state, i.e., if it occurs in nature, it has been changed or removed from its original environment, or both. For example, polynucleotide or a polypeptide naturally present in a living organism is not "isolated," but the same polynucleotide or polypeptide separated from the coexisting materials of its natural state is "isolated", as the term is employed herein.

"Polynucleotide(s)" generally refers to any polyribonucleotide or polydeoxribonucleotide, which may be unmodified RNA or DNA or modified RNA or DNA. "Polynucleotide(s)" include, without limitation, single-and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded, or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide (s)" includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques which are well known to the art. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains and the amino or carboxyl termini. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins such as arginylation, and ubiquitination. See, for instance, *PROTEINS—STRUCTURE AND MOLECULAR PROPERTIES*, 2nd Ed., T. E. Creighton, W. H. Freeman and Company, New York (1993) and Wold, F., Posttranslational Protein Modifications: Perspectives and Prospects, pgs. 1–12 in *POSTTRANSLATIONAL COVALENT MODIFICATION OF PROTEINS*, B. C. Johnson, Ed., Academic Press, New York (1983); Seifter et al., *Meth. Enzymol.* 182:626–646 (1990) and Rattan et al., *Protein Synthesis: Posttranslational Modifications and Aging*, Ann. N.Y. Acad. Sci. 663: 48–62 (1992). Polypeptides may be branched or cyclic, with or without branching. Cyclic, branched and branched circular polypeptides may result from post-translational natural processes and may be made by entirely synthetic methods, as well.

"Variant(s)" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

DESCRIPTION OF THE INVENTION

The invention relates to novel spoIIIE polypeptides and polynucleotides as described in greater detail below. In particular, the invention relates to polypeptides and polynucleotides of a novel spoIIIE gene of *Staphylococcus aureus*, which is related by amino acid sequence homology to *B. subtilis* spoIIE polypeptide. The invention relates especially to spoIIIE having the nucleotide and amino acid sequences set out in FIG. 1 and FIG. 2 respectively, and to the spoIIIE nucleotide sequences of the DNA in NCIMB Deposit No. 40771 and amino acid sequences encoded therin. The amino acid sequence of SEQ ID NO:2 AND SEQ ID NO:4 is the translated open reading frame sequence of SEQ ID NO:1 AND SEQ ID NO:3 and displays homology of 49% identity overall and 67% identity in the C-terminal conserved 500 amino acids to SpoIIIE from *B. subtilis*. The deduced amino acid sequence is based upon the use of TTG as a start codon, however, another amino acid sequence embodiment of the invention is based on an ATG start codon, and a futher embodoment is the DNA sequence of SEQ ID NO:1 AND SEQ ID NO:3 that encodes the amino acid sequence starting at Methionine number 43 of SEQ ID NO:2 AND SEQ ID NO:4. Thus, hererin, "SEQ ID NO:2 AND SEQ ID NO:4" means the amino acid sequence starting at Lysine number 1 or Methionine number 43. Also, herein, "SEQ ID NO:1 AND SEQ ID NO:3" means the polynucleotide starting at Thymine number 1 or Adenine number 127.

Techniques are available to evaluate temporal gene expression in bacteria, particularly as it applies to viability under laboratory and host infection conditions. A number of methods can be used to identify genes which are essential to survival per se, or essential to the establishment and/or maintenance of an infection. Identification of expression of a sequence by one of these methods yields additional information about its function and assists in the selection of such sequence for further development as a screening target. Briefly, these approaches include, for example:

1) Signature Tagged Mutagenesis (STM)

This technique is described by Hensel et al, *Science* 269: 400–403(1995), the contents of which is incorporated by reference for background purposes. Signature tagged mutagenesis identifies genes necessary for the establishment/maintenance of infection in a given infection model.

The basis of the technique is the random mutagenesis of target organism by various means (e.g., transposons) such that unique DNA sequence tags are inserted in close proximity to the site of mutation. The tags from a mixed population of bacterial mutants and bacteria recovered from an infected hosts are detected by amplification, radiolabeling and hybridization analysis. Mutants attenuated in virulence are revealed by absence of the tag from the pool of bacteria recovered from infected hosts.

In *Staphylococcus aureus*, because the transposon system is less well developed, a more efficient way of creating the tagged mutants is to use the insertion-duplication mutagenesis technique as described by Morrison et al., *J. Bacteriol.* 159:870 (1984) the contents of which is incorporated by reference for background purposes.

2) In Vivo Expression Technology (IVET)

This technique is described by Camilli et al., *Proc. Nat'l. Acad. Sci. USA.* 91:2634–2638 (1994) and Mahan et al., *Infectious Agents and Diseases* 2:263–268 (1994), the contents of each of which is incorporated by reference for background purposes. IVET identifies genes up-regulated during infection when compared to laboratory cultivation, implying an important role in infection. Sequences identified by this technique are implied to have a significant role in infection establishment/maintenance.

In this technique random chromosomal fragments of target organism are cloned upstream of a promoter-less reporter gene in a plasmid vector. The pool is introduced into a host and at various times after infection bacteria may be recovered and assessed for the presence of reporter gene expression. The chromosomal fragment carried upstream of an expressed reporter gene should carry a promoter or portion of a gene normally upregulated during infection. Sequencing upstream of the reporter gene allows identification of the up regulated gene.

3) Differential display

This technique is described by Chuang et al, *J. Bacteriol.* 175:2026–2036 (1993), the contents of which is incorporated by reference for background purposes. This method identifies those genes which are expressed in an organism by identifying mRNA present using randomly-primed RT-PCR. By comparing pre-infection and post infection profiles, genes up and down regulated during infection can be identified and the RT-PCR product sequenced and matched to library sequences.

4) Generation of conditional lethal mutants by transposon mutagenesis.

This technique, described by de Lorenzo, V. et al., *Gene* 123:17–24 (1993); Neuwald, A. F. et al., *Gene* 125: 69–73 (1993); and Takiff, H. E. et al.,*J. Bacteriol.* 174:1544–1553 (1992), the contents of which is incorporated by reference for background purposes, identifies genes whose expression are essential for cell viability.

In this technique transposons carrying controllable promoters, which provide transcription outward from the transposon in one or both directions, are generated. Random insertion of these transposons into target organisms and subsequent isolation of insertion mutants in the presence of inducer of promoter activity ensures that insertions which separate promoter from coding region of a gene whose expression is essential for cell viability will be recovered. Subsequent replica plating in the absence of inducer identifies such insertions, since they fail to survive. Sequencing of the flanking regions of the transposon allows identification of site of insertion and identification of the gene disrupted. Close monitoring of the changes in cellular processes/morphology during growth in the absence of inducer yields information on likely function of the gene. Such monitoring could include flow cytometry (cell division, lysis, redox potential, DNA replication), incorporation of radiochemically labeled precursors into DNA, RNA, protein, lipid, peptidoglycan, monitoring reporter enzyme gene fusions which respond to known cellular stresses.

5) Generation of conditional lethal mutants by chemical mutagenesis.

This technique is described by Beckwith, J., *Methods in Enzymology* 204: 3–18(1991), the contents of which are incorporated herein by reference for background purposes. In this technique random chemical mutagenesis of target organism, growth at temperature other than physiological temperature (permissive temperature) and subsequent replica plating and growth at different temperature (e.g., 42° C. to identify ts, 25° C. to identify cs) are used to identify those isolates which now fail to grow (conditional mutants). As above close monitoring of the changes upon growth at the non-permissive temperature yields information on the function of the mutated gene. Complementation of conditional lethal mutation by library from target organism and sequencing of complementing gene allows matching with library sequences.

Each of these techniques may have advantages or disadvantage depending on the particular application. The skilled artisan would choose the approach that is the most relevant with the particular end use in mind. For example, some genes might be recognised as essential for infection but in reality are only necessary for the initiation of infection and so their products would represent relatively unattractive targets for antibacterials developed to cure established and chronic infections.

6) RT-PCR

Bacterial messenger RNA, preferably that of *Staphylococcus aureus* is isolated from bacterial infected tissue, e.g., 48 hour murine lung infections, and the amount of each mRNA species assessed by reverse transcription of the RNA sample primed with random hexanucleotides followed by PCR with gene specific primer pairs. The determination of the presence and amount of a particular mRNA species by quantification of the resultant PCR product provides information on the bacterial genes which are transcribed in the infected tissue. Analysis of gene transcription can be carried out at different times of infection to gain a detailed knowledge of gene regulation in bacterial pathogenesis allowing for a clearer understanding of which gene products represent targets for screens for novel antibacterials. Because of the gene specific nature of the PCR primers employed it should be understood that the bacterial mRNA preparation need not be free of mammalian RNA. This allows the investigator to carry out a simple and quick RNA preparation from infected tissue to obtain bacterial mRNA species which are very short lived in the bacterium (in the order of 2 minute halflives). Optimally the bacterial mRNA is prepared from infected murine lung tissue by mechanical disruption in the presence of TRIzole (GIBCO-BRL) for very short periods of time, subsequent processing according to the manufacturers of TRIzole reagent and DNAase treatment to remove contaminating DNA. Preferably the process is optimized by finding those conditions which give a maximum amount of bacterial 16S ribosomal RNA, preferably that of *Staphylococcus aureus* as detected by probing Northerns with a suitably labeled sequence specific oligonucleotide probe. Typically, a 5' dye labelled primer is used in each PCR primer pair in a PCR reaction which is terminated optimally between 8 and 25 cycles. The PCR products are separated on 6% polyacrylamide gels with detection and quantification using GeneScanner (manufactured by ABI).

Use of the of these technologies when applied to the sequences of the invention enables ready identification of bacterial proteins expressed during infection, inhibitors of which would have utility in anti-bacterial therapy.

Deposited Materials

A deposit containing a *Staphylococcus aureus* WCUH 29 strain has been deposited with the National Collections of Industrial and Marine Bacteria Ltd. (NCIMB), 23 St. Machar Drive, Aberdeen AB2 1RY, Scotland on 11 Sep. 1995 and assigned NCIMB Deposit No. 40771. The *Staphylococcus aureus* strain deposit is referred to herein as "the deposited strain" or as "the DNA of the deposited strain."

The deposited material is a strain that contains the full length spoIIIE DNA, referred to as "NCIMB 40771" upon deposit.

The sequence of the polynucleotides contained in the deposited material, as well as the amino acid sequence of the polypeptide encoded thereby, are controlling in the event of any conflict with any description of sequences herein.

The deposit has been made under the terms of the Budapest Treaty on the International Recognition of the Deposit of Micro-organisms for Purposes of Patent Procedure. The strain will be irrevocably and without restriction or condition released to the public upon the issuance of a patent. The deposit is provided merely as convenience to those of skill in the art and is not an admission that a deposit is required for enablement, such as that required under 35 U.S.C. §112.

A license may be required to make, use or sell the deposited materials, and no such license is hereby granted.

Polypeptides

The polypeptides of the invention include the polypeptide of FIG. 2 [SEQ ID NO:2 AND SEQ ID NO:4] (in particular the mature polypeptide) as well as polypeptides and fragments, particularly those which have the biological activity of spoIIIE, and also those which have at least 70% identity to the polypeptide of FIG. 2 [SEQ ID NO:2 AND SEQ ID NO:4] or the relevant portion, preferably at least 80% identity to the polypeptide of FIG. 2 [SEQ ID NO:2 AND SEQ ID NO:4], and more preferably at least 90% similarity (more preferably at least 90% identity) to the polypeptide of FIG. 2 [SEQ ID NO:2 AND SEQ ID NO:4] and still more preferably at least 95% similarity (still more preferably at least 95% identity) to the polypeptide of FIG. 2 [SEQ ID NO:2 AND SEQ ID NO:4] and also include portions of such polypeptides with such portion of the polypeptide generally containing at least 30 amino acids and more preferably at least 50 amino acids.

Variants that are fragments of the polypeptides of the invention may be employed for producing the corresponding full-length polypeptide by peptide synthesis; therefore, these variants may be employed as intermediates for producing the full-length polypeptides. Variants that are fragments of the polynucleotides of the invention may be used to synthesize full-length polynucleotides of the invention.

A fragment is a variant polypeptide having an amino acid sequence that entirely is the same as part but not all of the amino acid sequence of the aforementioned polypeptides. As with spoIIIE polypeptides fragments may be "freestanding," or comprised within a larger polypeptide of which they form a part or region, most preferably as a single continuous region, a single larger polypeptide.

Preferred fragments include, for example, truncation polypeptides having a portion of the amino acid sequence of FIG. 2 [SEQ ID NO:2 AND SEQ ID NO:4], or of variants thereof, except for deletion of a continuous series of residues that includes the amino terminus, or a continuous series of residues that includes the carboxyl terminus or deletion of two continuous series of residues, one including the amino terminus and one including the carboxyl terminus. Degradation forms of the polypeptides of the invention in a host cell, particularly a *Staphylococcus aureus* are also preferred. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Also preferred are biologically active fragments which are those fragments that mediate activities of spoIIIE, including those with a similar activity or an improved activity, or with a decreased undesirable activity. Also included are those fragments that are antigenic or immunogenic in an animal, especially in a human.

Polynucleotides

Another aspect of the invention relates to isolated polynucleotides which encode the spoIIIE polypeptide having the deduced amino acid sequence of FIG. 2 [SEQ ID NO:2 AND SEQ ID NO:4] and polynucleotides closely related thereto and variants therto.

Using the information provided herein, such as the polynucleotide sequence set out in FIG. 1 [SEQ ID NO:1 AND SEQ ID NO:3], a polynucleotide of the invention encoding spoIIIE polypeptide may be obtained using standard cloning and screening, such as those for cloning and sequencing chromosomal DNA fragments from *Staphylococcus aureus*

WCUH 29 cells as starting material, followed by obtaining a full length clone. For example, to obtain a polynucleotide sequence of the invention, such as that sequence given in FIG. 1 [SEQ ID NO:1 AND SEQ ID NO:3], typically a library of clones of chromosomal DNA of *Staphylococcus aureus* WCUH 29 in *E.coli* or some other suitable host is probed with a radiolabeled oligonucleotide, preferably a 17-mer or longer, derived from a partial sequence. Clones carrying DNA identical to that of the probe can then be distinguished using stringent conditions. By sequencing the individual clones thus identified with sequencing primers designed from the original sequence it is then possible to extend the sequence in both directions to determine the full gene sequence. Conveniently such sequencing is performed using denatured double stranded DNA prepared from a plasmid clone. Suitable techniques are described by Maniatis, T., Fritsch, E. F. and Sambrook et al., *MOLECULAR CLONING, A LABORATORY MANUAL*, 2nd Ed.; Cold Spring Harbor Laboratory Press, Cold Spring Harbor, N.Y. (1989). (see Screening By Hybridization 1.90 and Sequencing Denatured Double-Stranded DNA Templates 13.70). Illustrative of the invention, the polynucleotide set out in FIG. 1 [SEQ ID NO:1 AND SEQ ID NO:3] was discovered in a DNA library derived from *Staphylococcus aureus* WCUH 29.

The DNA sequence thus obtained is set out in FIG. 1 [SEQ ID NO:1 AND SEQ ID NO:3]. It contains an open reading frame encoding a protein having about the number of amino acid residues set forth in FIG. 2 [SEQ ID NO:2 AND SEQ ID NO:4] with a deduced molecular weight that can be calculated using amino acid residue molecular weight values well known in the art. spoIIIE of the invention is structurally related to other proteins of the spo family, as shown by the results of sequencing the DNA encoding spoIIIE of the deposited strain. The protein exhibits greatest homology to *B. subtilis* spoIIE protein among known proteins. spoIIIE of FIG. 2 [SEQ ID NO:2 AND SEQ ID NO:4] has about 49% identity over its entire length with the amino acid sequence of *B. subtilis* spoIIE polypeptide.

Sequence of the invention may also be identical over its entire length to the coding sequence in FIG. 1 [SEQ ID NO:1 AND SEQ ID NO:3].

Also provided by the invention is the coding sequence for the mature polypeptide or a fragment thereof, by itself as well as the coding sequence for the mature polypeptide or a fragment in reading frame with other coding sequence, such as those encoding a leader or secretory sequence, a pre-, or pro- or prepro- protein sequence. The polynucleotide may also contain non-coding sequences, including for example, but not limited to non-coding 5' and 3' sequences, such as the transcribed, non-translated sequences, termination signals, ribosome binding sites, sequences that stabilize mRNA, introns, polyadenylation signals, and additional coding sequence which encode additional amino acids. For example, a marker sequence that facilitates purification of the fused polypeptide can be encoded. In certain embodiments of this aspect of the invention, the marker sequence is a hexa-histidine peptide, as provided in the pQE vector (Qiagen, Inc.) and described in Gentz et al, *Proc. Nat. Acad. Sci., USA* 86: 821–824 (1989), or an HA tag (Wilson et al, *Cell* 37: 767 (1984)). Polynucleotides of the invention also include, but are not limited to, polynucleotides comprising a structural gene and its naturally associated sequences that control gene expression.

In accordance with the foregoing, the term "polynucleotide encoding a polypeptide" as used herein encompasses polynucleotides which include a sequence encoding a polypeptide of the invention, particularly bacterial, and more particularly the *Staphylococcus aureus* spoIIIE having the amino acid sequence set out in FIG. 2 [SEQ ID NO:2 AND SEQ ID NO:4]. The term encompasses polynucleotides that include a single continuous region or discontinuous regions encoding the polypeptide (for example, interrupted by integrated phage or insertion sequence or editing) together with additional regions, that also may contain coding and/or non-coding sequences.

The invention further relates to variants of the herein above described polynucleotides which encode for variants of the polypeptide having the deduced amino acid sequence of FIG. 2 [SEQ ID NO:2 AND SEQ ID NO:4].

Further particularly preferred embodiments are polynucleotides encoding spoIIIE variants, which have the amino acid sequence of spoIIIE polypeptide of FIG. 2 [SEQ ID NO:2 AND SEQ ID NO:4] in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of spoIIIE.

Further preferred embodiments of the invention are polynucleotides that are at least 50%, 60% or 70% identical over their entire length to a polynucleotide encoding spoIIIE polypeptide having the amino acid sequence set out in FIG. 2 [SEQ ID NO:2 AND SEQ ID NO:4], and polynucleotides which are complementary to such polynucleotides. Alternatively, most highly preferred are polynucleotides that comprise a region that is at least 80% identical over their entire length to a polynucleotide encoding spoIIIE polypeptide of the *Staphylococcus aureus* DNA of the deposited strain and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments in this respect, moreover, are polynucleotides which encode polypeptides which retain substantially the same biological function or activity as the mature polypeptide encoded by the DNA of FIG. 1 [SEQ ID NO:1 AND SEQ ID NO:3].

The invention further relates to polynucleotides that hybridize to the herein above-described sequences. In this regard, the invention especially relates to polynucleotides which hybridize under stringent conditions to the herein above-described polynucleotides. As herein used, the terms "stringent conditions" and a "stringent hybridization conditions" mean hybridization will occur only if there is at least 95% and preferably at least 97% identity between the sequences. An example of stringent hybridization conditions is overnight incubation at 42° C. in a solution comprising: 50% formamide, 5× SSC (150 mM NaCl, 15 mM trisodium citrate), 50 mM sodium phosphate (pH7.6), 5× Denhardt's solution, 10% dextran sulfate, and 20 micrograms/ml denatured, sheared salmon sperm DNA, followed by washing the filters in 0.1× SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein, the disclosure of which is hereby incorporated in its entirety by reference.

The invention also provides a polynucleotide consisting essentially of a polynucleotide sequence obtainable by screening an appropriate library containing the complete gene for a polynucleotide sequence set forth in SEQ ID NO:1 AND SEQ ID NO:3 under stringent hybridization conditions with a probe having the sequence of said polynucleotide sequence set forth in SEQ ID NO:1 AND SEQ ID NO:3 or a fragment thereof; and isolating said DNA sequence. Fragments useful for obtaining such a polynucleotide include, for example, probes and primers described elsewhere herein.

As discussed additionally herein regarding polynucleotide assays of the invention, for instance, polynucleotides of the invention as discussed above, may be used as a hybridization probe for RNA, cDNA and genomic DNA to isolate full-length cDNAs and genomic clones encoding spoIIIE and to isolate cDNA and genomic clones of other genes that have a high sequence similarity to the spoIIIE gene. Such probes generally will comprise at least 15 bases. Preferably, such probes will have at least 30 bases and may have at least 50 bases. Particularly preferred probes will have at least 30 bases and will have 50 bases or less.

For example, the coding region of the spoIIIE gene may be isolated by screening using the known DNA sequence to synthesize an oligonucleotide probe. A labeled oligonucleotide having a sequence complementary to that of a gene of the invention is then used to screen a library of cDNA, genomic DNA or mRNA to determine which members of the library the probe hybridizes to.

The polynucleotides and polypeptides of the invention may be employed as research reagents and materials for discovery of treatments of and diagnostics for disease, particularly human disease, as further discussed herein relating to polynucleotide assays, inter alia.

Polynucleotides of the invention that are oligonucleotides derived from the sequences of SEQ ID NOS:1 and 2 may be used in the processes herein as described, but preferably for PCR, to determine whether or not the polynucleotides identified herein in whole or in part are transcribed in infected tissue. It is recognized that such sequences will also have utility in diagnosis of the stage of infection and type of infection the pathogen has attained.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Vectors, Host Cells, Expression

The invention also relates to vectors which comprise a polynucleotide or polynucleotides of the invention, host cells which are genetically engineered with vectors of the invention and the production of polypeptides of the invention by recombinant techniques. Cell-free translation systems can also be employed to produce such proteins using RNAs derived from the DNA constructs of the invention.

For recombinant production, host cells can be genetically engineered to incorporate expression systems or portions thereof or polynucleotides of the invention. Introduction of a polynucleotide into the host cell can be effected by methods described in many standard laboratory manuals, such as Davis et al., *BASIC METHODS IN MOLECULAR BIOLOGY*, (1986) and Sambrook et al., *MOLECULAR CLONING: A LABORATORY MANUAL*, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as streptococci, staphylococci, *E. coli*, streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

A great variety of expression systems can be used to produce a polypeptide of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., *MOLECULAR CLONING, A LABORATORY MANUAL*,(supra).

For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding protein may be employed to regenerate active conformation when the polypeptide is denatured during isolation and or purification.

Diagnostic Assays

This invention is also related to the use of the spoIIIE polynucleotides of the invention for use as diagnostic reagents. Detection of spoIIIE in a eukaryote, particularly a mammal, and especially a human, will provide a diagnostic method for diagnosis of a disease. Eukaryotes (herein also "individual(s)"), particularly mammals, and especially humans, infected with an organism comprising the spoIIIE gene may be detected at the DNA level by a variety of techniques.

Nucleic acids for diagnosis may be obtained from an infected individual's cells and tissues, such as bone, blood, muscle, cartilage, and skin. Genomic DNA may be used directly for detection or may be amplified enzymatically by using PCR or other amplification technique prior to analysis. RNA or cDNA may also be used in the same ways. Using amplification, characterization of the strain of prokaryote present in a eukaryote, particularly a mammal, and especially a human, may be made by an analysis of the genotype of the prokaryote gene. Deletions and insertions can be detected by a change in size of the amplified product in comparison to the genotype of a reference sequence. Point mutations can be identified by hybridizing amplified DNA to labeled spoIIIE; polynucleotide sequences. Perfectly matched sequences can be distinguished from mismatched duplexes by RNase digestion or by differences in melting temperatures. DNA sequence differences may also be detected by alterations in the electrophoretic mobility of the DNA fragments in gels, with or without denaturing agents, or by direct DNA sequencing. See, e.g., Myers et al., *Science*, 230: 1242 (1985). Sequence changes at specific locations also may be revealed by nuclease protection assays, such as RNase and S1 protection or a chemical cleavage method. See, e.g., Cotton et al., *Proc. Natl. Acad. Sci., USA*, 85: 4397–4401 (1985).

Cells carrying mutations or polymorphisms in the gene of the invention may also be detected at the DNA level by a variety of techniques, to allow for serotyping, for example. For example, RT-PCR can be used to detect mutations. It is particularly preferred to used RT-PCR in conjunction with automated detection systems, such as, for example, GeneScan. RNA or cDNA may also be used for the same purpose, PCR or RT-PCR. As an example, PCR primers complementary to the nucleic acid encoding spoIIIE can be used to identify and analyze mutations These primers may be used for amplifying spoIIIE DNA isolated from a sample derived from an individual. The invention also provides these primers with 1, 2, 3 or 4 nucleotides removed from the 5' and/or the 3' end. The primers may be used to amplify the gene isolated from an infected individual such that the gene may then be subject to various techniques for elucidation of the DNA sequence. In this way, mutations in the DNA sequence may be detected and used to diagnose infection and to serotype or classify the infectious agent.

The invention provides a process for diagnosing, disease, preferably bacterial infections, more preferably infections by *Staphylococcus aureus* and most preferably disease, such as, infections of the upper respiratory tract (e.g. otitis media, bacterial tracheitis, acute epiglottitis, thyroiditis), lower respiratory (e.g. empyema, lung abscess),cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal & orbital cellulitis, darcryocystitis), kidney and urinary tract (e.g. epididymitis, intrarenal and perinephric abscess, toxic shock syndrome), skin (e.g. impetigo, folliculitis, cutaneous abscesses, cellulitis, wound infection, bacterial myositis) bone and joint (e.g. septic arthritis, osteomyelitis), comprising determining from a sample derived from an individual a increased level of expression of polynucleotide having the sequence of FIG. 1 [SEQ ID NO:1]. Increased or decreased expression of spoIIIE polynucleotide can be measured using any on of the methods well known in the art for the quantation of polynucleotides, such as, for example, amplification, PCR, RT-PCR, RNase protection, Northern blotting and other hybridization methods.

In addition, a diagnostic assay in accordance with the invention for detecting over-expression of spoIIIE protein compared to normal control tissue samples may be used to detect the presence of an infection, for example. Assay techniques that can be used to determine levels of a protein, in a sample derived from a host are well-known to those of skill in the art. Such assay methods include radioimmunoassays, competitive-binding assays, Western Blot analysis and ELISA assays.

Antibodies

The polypeptides of the invention or variants thereof, or cells expressing them can be used as an immunogen to produce antibodies immunospecific for such polypeptides. "Antibodies" as used herein includes monoclonal and polyclonal antibodies, chimeric, single chain, simianized antibodies and humanized antibodies, as well as Fab fragments, including the products of an Fab immunolglobulin expression library.

Antibodies generated against the polypeptides of the invention can be obtained by administering the polypeptides or epitope-bearing fragments, analogues or cells to an animal, preferably a nonhuman, using routine protocols. For preparation of monoclonal antibodies, any technique known in the art which provides antibodies produced by continuous cell line cultures can be used. Examples include various techniques, such as those in Kohler, G. and Milstein, C., *Nature* 256: 495–497 (1975); Kozbor et al, *Imununology Today* 4: 72 (1983); Cole et al., pg. 77–96 in *MONOCLONAL ANTIBODIES AND CANCER THERAPY*, Alan R. Liss, Inc. (1985).

Techniques for the production of single chain antibodies (U.S. Pat. No. 4,946,778) can be adapted to produce single chain antibodies to polypeptides of this invention. Also, transgenic mice, or other organisms such as other mammals, may be used to express humanized antibodies.

Alternatively phage display technology could be utilized to select antibody genes with binding activities towards the polypeptide either from repertoires of PCR amplified v-genes of lymphocytes from humans screened for possessing anti-Fbp or from naive libraries (McCafferty, J. et al., (1990), *Nature* 348, 552–554; Marks, J. et al., (1992) *Biotechnology* 10, 779–783). The affinity of these antibodies can also be improved by chain shuffling (Clackson, T. et al., (1991) *Nature* 352, 624–628).

If two antigen binding domains are present each domain may be directed against a different epitope-termed 'bispecific' antibodies.

The above-described antibodies may be employed to isolate or to identify clones expressing the polypeptides to purify the polypeptides by affinity chromatography.

Thus, among others, antibodies against spoIIIE may be employed to treat infections, particularly bacterial infections and especially disease, such as, infections of the upper respiratory tract (e.g. otitis media, bacterial tracheitis, acute epiglottitis, thyroiditis), lower respiratory (e.g. empyema, lung abscess),cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal & orbital cellulitis, darcryocystitis), kidney and urinary tract (e.g. epididymitis, intrarenal and perinephric abscess, toxic shock syndrome), skin (e.g. impetigo, folliculitis, cutaneous abscesses, cellulitis, wound infection, bacterial myositis) bone and joint (e.g. septic arthritis, osteomyelitis).

Polypeptide variants include antigenically, epitopically or immunologically equivalent variants which form a particular aspect of this invention. The term "antigenically equivalent derivative" as used herein encompasses a polypeptide or its equivalent which will be specifically recognised by certain antibodies which, when raised to the protein or polypeptide according to the invention, interfere with the immediate physical interaction between pathogen and mammalian host. The term "immunologically equivalent derivative" as used herein encompasses a peptide or its equivalent which when used in a suitable formulation to raise antibodies in a vertebrate, the antibodies act to interfere with the immediate physical interaction between pathogen and mammalian host.

The polypeptide, such as an antigenically or immunologically equivalent derivative or a fusion protein thereof is used as an antigen to immunize a mouse or other animal such as a rat or chicken. The fusion protein may provide stability to the polypeptide. The antigen may be associated, for example by conjugation, with an immunogenic carrier protein for example bovine serum albumin (BSA) or keyhole limpet haemocyanin (KLH). Alternatively a multiple antigenic peptide comprising multiple copies of the protein or polypeptide, or an antigenically or immunologically equivalent polypeptide thereof may be sufficiently antigenic to improve immunogenicity so as to obviate the use of a carrier.

Preferably the antibody or variant thereof is modified to make it less immunogenic in the individual. For example, if the individual is human the antibody may most preferably be "humanized"; where the complimentarity determining region(s) of the hybridoma-derived antibody has been transplanted into a human monoclonal antibody, for example as described in Jones, P. et al. (1986), Nature 321, 522–525 or Tempest et al.,(1991) Biotechnology 9, 266–273.

The use of a polynucleotide of the invention in genetic immunization will preferably employ a suitable delivery method such as direct injection of plasmid DNA into muscles (Wolff et al., Hum Mol Genet 1992, 1:363, Manthorpe et al., Hum. Gene Ther. 1963:4, 419), delivery of DNA complexed with specific protein carriers (Wu et al., J Biol Chem 1989:264, 16985), coprecipitation of DNA with calcium phosphate (Benvenisty & Reshef, PNAS, 1986:83, 9551), encapsulation of DNA in various forms of liposomes (Kaneda et al., Science 1989:243, 375), particle bombardment (Tang et al., Nature 1992, 356:152, Eisenbraun et al., DNA Cell Biol 1993, 12:791) and in vivo infection using cloned retroviral vectors (Seeger et al., PNAS 1984:81, 5849).

Polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See, e.g., Coligan et al, *Current Protocols in Immunology* 1(2): Chapter 5 (1991).

Antagonists and Agonists—Assays and Molecules

The invention also provides a method of screening compounds to identify those which enhance (agonist) or block (antagonist) the action of spoIIIE polypeptides or polynucleotides.

For example, to screen for agonists or antagoists, a synthetic reaction mix, a cellular compartment, such as a membrane, cell envelope or cell wall, or a preparation of any thereof, comprising spoIIIE polypeptide and a labeled substrate of such polypeptide is incubated in the absence or the presence of a candidate molecule which may be a spoIIIE agonist or antagonist. The ability of the candidate molecule to agonize or antagonize the spoIIIE polypeptide is reflected in decreased binding of the labeled ligand or decreased production of product from such substrate. Molecules which bind gratuitously, i.e., without inducing the effects of spoIIIE are most likely to be good antagonists. Molecules that bind well and increase the rate of product production from substrate are agonists. The rate or level of production of product from substrate may be enhanced by using a reporter system. Reporter systems that may be useful in this regard include but are not limited to colorimetric labeled substrate converted into product, a reporter gene that is responsive to changes in spoIIIE activity, and binding assays known in the art.

Another example of an assay for spoIIIE antagonists is a competitive assay that combines spoIIIE and a potential antagonist with spoIIIE-binding molecules, recombinant spoIIIE binding molecules, natural substrates or ligands, or substrate or ligand mimetics, under appropriate conditions for a competitive inhibition assay. spoIIIE can be labeled, such as by radioactivity or a colorimetric compound, such that the number of spoIIIE molecules bound to a binding molecule or converted to product can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a binding molecule, without inducing spoIIIE-induced activities, thereby preventing the action of spoIIIE by excluding spoIIIE from binding.

Potential antagonists include a small molecule which binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano, *J. Neurochem.* 56: 560 (1991); *OLIGODEOXY-NUCLEOTIDES AS ANTISENSE INHIBITORS OF GENE EXPRESSION*, CRC Press, Boca Raton, Fla. (1988), for a description of these molecules). Preferred potential antagonists include compounds related to and variants of spoIIIE.

In a particular aspect the invention provides the use of the polypeptide, polynucleotide or inhibitor of the invention to interfere with the initial physical interaction between a pathogen and mammalian host responsible for sequelae of infection. In particular the molecules of the invention may be used: i) in the prevention of adhesion of bacteria, in particular gram positive bacteria, to mammalian extracellular matrix proteins on in-dwelling devices or to extracellular matrix proteins in wounds; ii) to block spoIIIE protein mediated mammalian cell invasion by, for example, initiating phosphorylation of mammalian tyrosine kinases (Rosenshine et al, *Infect. Immun.* 60:2211 (1992); iii) to block bacterial adhesion between mammalian extracellular matrix proteins and bacterial spoIIIE proteins which mediate tissue damage; iv) to block the normal progression of pathogenesis in infections initiated other than by the implantation of in-dwelling devices or by other surgical techniques.

Each of the DNA sequences provided herein may be used in the discovery and development of antibacterial compounds. The encoded protein upon expression can be used as a target for the screening of antibacterial drugs. Additionally, the DNA sequences encoding the amino terminal regions of the encoded protein or Shine-Delgarno or other translation facilitating sequences of the respective RNA can be used to construct antisense sequences to control the expression of the coding sequence of interest.

This invention provides a method of screening drugs to identify those which interfere with the mechanism of action of the SpoIIIE protein such that it is inhibited, the method comprising contacting the SpoIIIE protein with the drug and measuring the inhibition of SpoIIIE activity. The polypeptide in any of the forms described above, purified using any of the methods described above, can be used to configure an in vitro assay based on its mechanism of action, for example in the presence of purified bacterial membranes or vesicles or synthetic phospholipid membrane mimics or in the appropriate enzyme buffer if membranes are not required and including the incorporation of additional macromolecular or low molecular weight cofactors which are either necessary for, or potentate, the activities of SpoIIIE protein.

Examples of assays relating to the invention are set forth below:

(1) Nucleoside 5'-triphosphate Binding and 5'-triphosphatase Activity. The binding of nucleoside 5'-triphosphates (NTPs), such as adenosine 5'-triphosphate (ATP) to, and the subsequent hydrolysis by, SpoIIIE protein provides for two potential in vitro assay formats. Nucleotide binding assays may be based on homogeneous or heterogeneous measurements and using radioactively labelled nucleotide (photoaffinity cross linking, gel filtration, filter binding) and using a molecular optical signal to report upon, and monitor the extent of, the binding of nucleotide or of a fluorescent/chromophoric nucleotide derivative (fluorescence intensity, anisotropy, fluctuation correlation and energy transfer measurements, absorbance and circular dichroism measurements). The ability of SpoIIIE protein, either in the presence or absence of additional cofactors, to catalyse nucleotide hydrolysis is monitored by the change in substrate (NTP) and/or product (NDP, inorganic phosphate) concentration using either direct (radioactivity, colorimetric) or coupled enzyme formats.

(2) Nucleic Acid Binding and Vectorial Translocation Activity. The interaction of SpoIIIE protein with either natural or synthetic oligonucleotide or polynucleotide ribonucleic acids (RNA) or deoxyribonucleic acids (DNA), or analogues thereof, can be assayed using materials and methods analogous to those described in (1) above for the binding of nucleoside triphosphates and which are obvious to a practitioner skilled in the art of protein biochemistry and nucleic acid molecular biology. The DNA binding site sequence may be identified by making random pools of oligonucleotides and identifying the sequence of the ones which bind iteratively, or by recovery, amplification and sequencing of the DNA. Furthermore, the vectorial motion of nucleic acids due to the action of SpoIIIE through a well defined physical boundary (e.g a lipid vesicle, biological membrane), either in the presence or absence of additional macromolecular and low molecular weight cofactors, can be measured using either a solution based or heterogeneous separation format linked to an optical or radioactive measurement. For example, an assay could use vesicles with a pH gradient across the boundary and a fluorescein-labelled nucleic acid. The translocation of the nucleic acid into the vesicle due to the action of SpoIIIE would result in a measurable quenching of the fluorescein fluorescence.

(3) Protein: Protein Interactions: The measurement of the interaction of SpoIIIE protein with additional proteins or peptides, either within a lipid-based membrane system or in solution, provides for a potential assay format. Heterogeneous assays encompassing the use of an immunoassay or surface-coating format in conjunction with either radiolabelled or optically labelled proteins and components are envisaged. The interaction of unlabelled SpoIIIE with other polypeptides can also be observed directly using surface plasmon resonance technology in optical biosensor devices. This method is particularly useful for measuring interactions with larger (>5 kDa) polypeptides and can be adapted to screen for inhibitors of the protein-protein interaction. Solution-based homogeneous assays using fluorescently-labelled components may be configured to report on changes in fluorescence intensity, fluorescence anisotropy, fluorescence energy transfer or correlation fluctuations in intensity as a result of the binding interaction. Binding proteins useful in these types of assay may be identified by 'ligand fishing' using, for example, optical biosensor methods and bacterial extracts followed by affinity capture or chromatography on immobilised SpoIIIE. Optionally, derivatives of SpoIIIE with aminoacid sequences altered to improve aqueous solubility may be employed. Solution-phase capture of SpoIIIE binding proteins may be carried out by mixing soluble SpoIIIE with, for example, a detergent extract and reisolating a complex by use of anti-SpoIIIE antibodies or by tagging the SpoIIIE with, for example, Biotin and capture on immobilised avidin or streptavidin. Following elution of binding proteins from immobilised SpoIIIE using salt, pH changes or chaotropic agents, the eluted protein products may be separated using high-resolution methods such as reverse-phase high performance liquid chromatography and the individual polypeptides characterised by N-terminal aminoacid sequencing and/or mass mapping (mass spectrometry combined with molecular ion weight matching against a protein database.

(4) Microsocopy: pure SpoIIIE protein is used to raise antibodies in mice or rabbits or other suitable animal host, which antibodies are conjugated to gold particles attached to a secondary antibody. Actively dividing cells are sampled, the gold conjugate is added, and the sample prepared for electon microscopy using standard techniques and visualise to see the localisation of the protein and any effect of test drug.

The antagonists and agonists may be employed for instance to inhibit disease, such as, infections of the upper respiratory tract (e.g. otitis media, bacterial tracheitis, acute epiglottitis, thyroiditis), lower respiratory (e.g. empyema, lung abscess),cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal & orbital cellulitis, darcryocystitis), kidney and urinary tract (e.g. epididymitis, intrarenal and perinephric abscess, toxic shock syndrome), skin (e.g. impetigo, folliculitis, cutaneous abscesses, cellulitis, wound infection, bacterial myositis) bone and joint (e.g. septic arthritis, osteomyelitis).

Vaccines

Another aspect of the invention relates to a method for inducing an immunological response in an individual, particularly a mammal which comprises inoculating the individual with spoIIIE, or a fragment or variant thereof, adequate to produce antibody to protect said individual from infection, particularly bacterial infection and most particularly *Staphylococcus aureus* infections. Yet another aspect of the invention relates to a method of inducing immunological response in an individual which comprises, through gene therapy, delivering gene encoding spoIIIE, or a fragment or a variant thereof, for expressing spoIIIE, or a fragment or a variant thereof in vivo in order to induce an immunological response to produce antibody to protect said individual from disease.

A further aspect of the invention relates to an immunological composition which, when introduced into a host capable or having induced within it an immunological response, induces an immunological response in such host to a spoIIIE or protein coded therefrom, wherein the composition comprises a recombinant spoIIIE or protein coded therefrom comprising DNA which codes for and expresses an antigen of said spoIIIE or protein coded therefrom.

The spoIIIE or a fragment thereof may be fused with co-protein which may not by itself produce antibodies, but is capable of stabilizing the first protein and producing a fused protein which will have immunogenic and protective properties. Thus fused recombinant protein, preferably further comprises an antigenic co-protein, such as Glutathione-S-transferase (GST) or beta-galactosidase, relatively large co-proteins which solubilise the protein and facilitate production and purification thereof. Moreover, the co-protein may act as an adjuvant in the sense of providing a generalized stimulation of the immune system. The co-protein may be attached to either the amino or carboxy terminus of the first protein.

Provided by this invention are compositions, particularly vaccine compositions, and methods comprising the polypeptides or polynucleotides of the invention and immunostimulatory DNA sequences, such as those described in Sato, Y. et al. Science 273: 352 (1996).

Also, provided by this invention are methods using the described polynucleotide or particular fragments thereof which have been shown to encode non-variable regions of bacterial cell surface proteins in DNA constructs used in such genetic immunization experiments in animal models of infection with *Staphylococcus aureus* will be particularly useful for identifying protein epitopes able to provoke a prophylactic or therapeutic immune response. It is believed that this approach will allow for the subsequent preparation of monoclonal antibodies of particular value from the requisite organ of the animal successfully resisting or clearing infection for the development of prophylactic agents or therapeutic treatments of bacterial infection, particularly *Staphylococcus aureus* infections, in mammals, particularly humans.

The polypeptide may be used as an antigen for vaccination of a host to produce specific antibodies which protect against invasion of bacteria, for example by blocking adherence of bacteria to damaged tissue. Examples of tissue damage include wounds in skin or connective tissue caused e.g. by mechanical, chemical or thermal damage or by implantation of indwelling devices, or wounds in the mucous membranes, such as the mouth, mammary glands, urethra or vagina.

The invention also includes a vaccine formulation which comprises the immunogenic recombinant protein together with a suitable carrier. Since the protein may be broken down in the stomach, it is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostats and solutes which render the formulation instonic with the bodily fluid, preferably the blood, of the individual; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

While the invention has been described with reference to certain spoIIIE, it is to be understood that this covers fragments of the naturally occurring protein and similar proteins with additions, deletions or substitutions which do not substantially affect the immunogenic properties of the recombinant protein.

Compositions, Kits and Administration

The invention also relates to compositions comprising the polynucleotide or the polypeptides discussed above or the agonists or antagonists. The polypeptides of the invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration. The invention further relates to diagnostic and pharmaceutical packs and kits comprising one or more containers filled with one or more of the ingredients of the aforementioned compositions of the invention.

Polypeptides and other compounds of the invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

In-dwelling devices include surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, continuous ambulatory peritoneal dialysis (CAPD) catheters, etc.

The composition of the invention may be administered by injection to achieve a systemic effect against relevant bacteria shortly before insertion of an in-dwelling device. Treatment may be continued after surgery during the in-body time of the device. In addition, the composition could also be used to broaden perioperative cover for any surgical technique to prevent bacterial wound infections, especially *Staphylococcus aureus* wound infections.

Many orthopaedic surgeons consider that humans with prosthetic joints should be considered for antibiotic prophylaxis before dental treatment that could produce a bacteremia. Late deep infection is a serious complication sometimes leading to loss of the prosthetic joint and is accompanied by significant morbidity and mortality. It may therefore be possible to extend the use of the active agent as a replacement for prophylactic antibiotics in this situation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

Alternatively, the composition of the invention may be used to bathe an indwelling device immediately before insertion. The active agent will preferably be present at a concentration of 1 μg/ml to 10 mg/ml for bathing of wounds or indwelling devices.

A vaccine composition is conveniently in injectable form. Conventional adjuvants may be employed to enhance the immune response. A suitable unit dose for vaccination is 0.5–5 μg/kg of antigen, and such dose is preferably administered 1–3 times and with an interval of 1–3 weeks. With the indicated dose range, no adverse toxicological effects will be observed with the compounds of the invention which would preclude their administration to suitable individuals.

The antibodies described above may also be used as diagnostic reagents to detect the presence of bacteria containing the spoIIIE protein.

EXAMPLES

The examples below are carried out using standard techniques, which are well known and routine to those of skill in the art, except where otherwise described in detail. The examples are illustrative, but do not limit the invention.

Example 1

Isolation of DNA Coding for a Novel SpoIIIE Protein from *S. aureus* WCUH 29

The polynucleotide having the DNA sequence given in SEQ ID NO:1 was obtained from a library of clones of chromosomal DNA of *S.aureus* WCUH 29 in *E.coli*. Libraries may be prepared by routine methods, for example:

Methods 1 and 2

Total cellular DNA is isolated from *Staphylococcus aureus* strain WCUH29 (NCIMB 40771) according to standard procedures and size-fractionated by either of two methods.

Method 1.

Total cellular DNA is mechanically sheared by passage through a needle in order to size-fractionate according to standard procedures. DNA fragments of up to 11 kbp in size are rendered blunt by treatment with exonuclease and DNA polymerase, and EcoRI linkers added. Fragments are ligated into the vector Lambda ZapII that has been cut with EcoRI, the library packaged by standard procedures and *E.coli* infected with the packaged library. The library is amplified by standard procedures.

Method 2.

Total cellular DNA is partially hydrolysed with a combination of four restriction enzymes (RsaI, PalI, AluI and Bsh1235I) and size-fractionated according to standard procedures. EcoRI linkers are ligated to the DNA and the fragments then ligated into the vector Lambda ZapII that have been cut with EcoRI, the library packaged by standard procedures, and *E.coli* infected with the packaged library. The library is amplified by standard procedures.

What is claimed is:

1. An isolated polynucleotide comprising nucleotides 1 to 2317 set forth in SEQ ID NO:1.

2. An isolated polynucleotide encoding a polypeptide comprising the amino acids of SEQ ID NO:2.

3. A vector comprising the nucleotides of claim 1 or claim 2.

4. A host cell comprsing the vector of claim 3.

5. A process for producing a polypeptide comprising the step of expressing from the host cell of claim 3 a polypeptide encoded by said nucleotides.

6. A process for producing a cell which expresses a polypeptide comprising the step of transforming or transfecting the cell with the vector of claim 3 such that the cell expresses the polypeptide encoded by the nucleotides contained in the vector.

7. A probe comprising an isolated polynucleotide selected fromn the group consisting of: at least 30 bases of the polynucleotide sequence set forth in SEQ ID NO: 1 and at least 50 bases of the polynucleotide sequence set forth in SEQ ID NO: 1.

8. A probe consisting of an isolated polynucleotide selected from the group consisting of: at least 30 bases of the polynucleotide sequence set forth in SEQ ID NO: 1 and at least 50 bases of the polynucleotide sequence set forth in SEQ ID NO: 1.

9. A polynucleotide which is fully complemnntary to a polynucleotide of claim 1, 2, 7 and 8.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

(i) SEQUENCE CHARACTERISTICS:
   (A) LENGTH: 2367 base pairs
   (B) TYPE: nucleic acid
   (C) STRANDEDNESS: double
   (D) TOPOLOGY: linear (ii) MOLECULE TYPE: Genomic DNA (xi) SEQUENCE DESCRIPTION: SEQ ID NO:1:

| | | | | | | |
|---|---|---|---|---|---|---|
| TTGGCTCAAG | CAAAAAAGAA | ATCGACAGCT | AAGAAAAAAA | CAGCATCAAA | AAAAAGAACA | 60 |
| AATTCAAGGA | AAAAGAAGAA | TGATAATCCG | ATACGTTATG | TCATAGCTAT | TTTAGTAGTT | 120 |
| GTATTAATGG | TGTTGGGTGT | TTTCCAATTA | GGAATAATCG | GTCGTCTAAT | TGACAGCTTC | 180 |
| TTTAATTATT | TATTTGGGTA | CAGTAGATAT | TTAACATATA | TTTTAGTACT | CTTAGCAACT | 240 |
| GGTTTTATTA | CATACTCTAA | ACGTATTCCT | AAAACTAGAC | GAACGGCTGG | TTCGATTGTA | 300 |
| TTGCAAATTG | CATTGCTATT | TGTATCACAG | TTAGTTTTTC | ATTTTAATAG | TGGTATCAAA | 360 |
| GCTGAAAGAG | AACCTGTACT | TTCTTATGTA | TATCAGTCAT | ACCAACACAG | TCATTTTCCA | 420 |
| AATTTTGGTG | GCGGTGTATT | AGGTTTTTAT | TTATTAGAGT | TAAGCGTACC | TTTAATTTCA | 480 |
| TTATTTGGTG | TATGTATTAT | TACTATTTTA | TTATTATGCT | CAAGTGTTAT | TTTATTAACA | 540 |
| AACCATCAAC | ATCGTGATGT | TGCAAAAGTT | GCACTGGAAA | ATATAAAAGC | TTGGTTTGGT | 600 |
| TCATTTAATG | AAAAAATGTC | GGAAAGAAAC | CAAGAAAAAC | AATTGAAGCG | TGAAGAAAAA | 660 |
| GCGAGACTTA | AGAAGAACA | AAAGGCACGT | CAAAATGAAC | AGCCACAAAT | AAAAGATGTG | 720 |
| AGTGATTTTA | CGGAAGTGCC | TCAAGAAAGA | GATATTCCAA | TTTATGGGCA | TACTGAAAAT | 780 |
| GAAAGTAAAA | GCCAGTGTCA | ACCAAGTCGA | AAAAAACGAG | TGTTTGATGC | AGAGAATAGT | 840 |
| TCGAATAACA | TCGTAAATCA | TCAAGCAGAT | CAGCAAGAGC | AATTAACAGA | ACAAACTCAT | 900 |
| AACAGTGTTG | AAAGTGAAAA | CACTATTGAA | GAAGCTGGTG | AAGTTACGAA | TGTATCGTAT | 960 |
| GTTGTTCCAC | CGTTAACTTT | ACTTAATCAA | CCTGCAAAAC | AAAAAGCAAC | ATCTAAAGCT | 1020 |
| GAAGTACAAC | GTAAAGGACA | AGTACTAGAG | AATACATTAA | AAGATTTTGG | GGTAAATGCA | 1080 |
| AAAGTGACAC | AAATTAAAAT | TGGTCCTGCA | GTAACTCAAT | ATGAAATTCA | ACCAGCTCAA | 1140 |
| GGGGTTAAAG | TGAGTAAAAT | TGTAAACTTG | CATAATGATA | TTGCATTAGC | TTTAGCAGCA | 1200 |
| AAAGATGTTA | GAATCGAAGC | ACCAATACCT | GGTCGCTCTG | CAGTAGGTAT | TGAAGTGCCA | 1260 |
| AATGAGAAAA | TTTCATTAGT | TTCACTAAAA | GAAGTTTTAG | ATGAAAAATT | CCCGTCTAAT | 1320 |
| AATAAACTAG | AAGTTGGATT | AGGAAGAGAT | ATATCAGGTG | ATCCAATTAC | TGTTCCACTA | 1380 |
| AATGAAATGC | CACACTTATT | GGTGGCAGGA | TCGACGGGTA | GTGGTAAATC | TGTTTGTATA | 1440 |
| AATGGTATTA | TTACAAGTAT | TTTATTAAAT | GCTAAGCCGC | ATGAAGTTAA | ACTTATGTTA | 1500 |
| ATCGATCCGA | AAATGGTTGA | ACTAAATGTT | TATAACGGAA | TTCCACATTT | ATTAATTCCG | 1560 |
| GTTGTTACAA | ATCCTCATAA | AGCTGCTCAA | GCTTTAGAAA | AAATTGTAGC | TGAGATGGAA | 1620 |
| AGACGTTATG | ATTTATTCCA | ACATTCATCA | ACTAGAAATA | TTAAAGGTTA | TAACGAATTA | 1680 |
| ATCCGTAAGC | AAAATCAAGA | ATTAGATGAG | AAGCAACCAG | AATTACCTTA | TATCGTTGTT | 1740 |
| ATTGTAGATG | AGCTTGCAGA | TTTAATGATG | GTAGCTGGTA | AAGAAGTTGA | AAATGCGATT | 1800 |
| CAACGTATCA | CACAAATGGC | ACGTGCAGCA | GGTATACATT | TGATTGTAGC | AACACAAAGA | 1860 |
| CCTTCTGTGG | ATGTAATTAC | AGGTATCATT | AAAAATAACA | TTCCATCTAG | AATTGCTTTT | 1920 |
| GCTGTGAGTT | CTCAAACAGA | TTCAAGAACT | ATTATTGGTA | CTGGCGGCGC | AGAAAGTTA | 1980 |
| CTTGGTAAAG | GTGACATGTT | ATACGTTGGA | AATGGTGATT | CATCACAAAC | ACGTATTCAA | 2040 |
| GGGGCGTTTT | TAAGTGACCA | AGAGGTGCAA | GATGTTGTAA | ATTATGTAGT | AGAACAACAA | 2100 |

```
CAGGCAAATT ATGTAAAAGA AATGGAACCA GATGCACCAG TGGATAAATC GGAAATGAAA    2160

AGTGAAGATG CTTTATATGA TGAAGCGTAT TTGTTTGTTG TTGAACAACA AAAGGCAAGT    2220

ACATCATTGT TACAACGCCA ATTTAGAATT GGTTATAATA GAGCATCTAG GTTGATGGAT    2280

GATTTAGAAC GCAATCAGGT AATCGGTCCA CAAAAAGGAA GCAAGCCTAG ACAAGTTTTA    2340

ATAGATCTTA ATAATGACGA GGTGTAA                                      2367
```

( 2 ) INFORMATION FOR SEQ ID NO:2:

( i ) SEQUENCE CHARACTERISTICS:
        ( A ) LENGTH: 788 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Leu Ala Gln Ala Lys Lys Ser Thr Ala Lys Lys Lys Thr Ala Ser
  1               5                  10                  15

Lys Lys Arg Thr Asn Ser Arg Lys Lys Asn Asp Asn Pro Ile Arg
             20                  25                  30

Tyr Val Ile Ala Ile Leu Val Val Leu Met Val Leu Gly Val Phe
             35                  40                  45

Gln Leu Gly Ile Ile Gly Arg Leu Ile Asp Ser Phe Phe Asn Tyr Leu
 50                  55                  60

Phe Gly Tyr Ser Arg Tyr Leu Thr Tyr Ile Leu Val Leu Leu Ala Thr
 65                  70                  75                  80

Gly Phe Ile Thr Tyr Ser Lys Arg Ile Pro Lys Thr Arg Arg Thr Ala
             85                  90                  95

Gly Ser Ile Val Leu Gln Ile Ala Leu Leu Phe Val Ser Gln Leu Val
            100                 105                 110

Phe His Phe Asn Ser Gly Ile Lys Ala Glu Arg Glu Pro Val Leu Ser
            115                 120                 125

Tyr Val Tyr Gln Ser Tyr Gln His Ser His Phe Pro Asn Phe Gly Gly
            130                 135                 140

Gly Val Leu Gly Phe Tyr Leu Leu Glu Leu Ser Val Pro Leu Ile Ser
145                 150                 155                 160

Leu Phe Gly Val Cys Ile Ile Thr Ile Leu Leu Leu Cys Ser Ser Val
                165                 170                 175

Ile Leu Leu Thr Asn His Gln His Arg Asp Val Ala Lys Val Ala Leu
            180                 185                 190

Glu Asn Ile Lys Ala Trp Phe Gly Ser Phe Asn Glu Lys Met Ser Glu
            195                 200                 205

Arg Asn Gln Glu Lys Gln Leu Lys Arg Glu Glu Lys Ala Arg Leu Lys
            210                 215                 220

Glu Glu Gln Lys Ala Arg Gln Asn Glu Gln Pro Gln Ile Lys Asp Val
225                 230                 235                 240

Ser Asp Phe Thr Glu Val Pro Gln Glu Arg Asp Ile Pro Ile Tyr Gly
                245                 250                 255

His Thr Glu Asn Glu Ser Lys Ser Gln Cys Gln Pro Ser Arg Lys Lys
            260                 265                 270

Arg Val Phe Asp Ala Glu Asn Ser Ser Asn Asn Ile Val Asn His Gln
            275                 280                 285

Ala Asp Gln Gln Glu Gln Leu Thr Glu Gln Thr His Asn Ser Val Glu
            290                 295                 300
```

| | | | | | | | | | | | | | | | |
|---|---|---|---|---|---|---|---|---|---|---|---|---|---|---|---|
| Ser 305 | Glu | Asn | Thr | Ile | Glu 310 | Glu | Ala | Gly | Glu | Val 315 | Thr | Asn | Val | Ser | Tyr 320 |
| Val | Val | Pro | Pro | Leu 325 | Thr | Leu | Leu | Asn | Gln 330 | Pro | Ala | Lys | Gln | Lys 335 | Ala |
| Thr | Ser | Lys | Ala 340 | Glu | Val | Gln | Arg | Lys 345 | Gly | Gln | Val | Leu | Glu 350 | Asn | Thr |
| Leu | Lys | Asp 355 | Phe | Gly | Val | Asn | Ala 360 | Lys | Val | Thr | Gln | Ile 365 | Lys | Ile | Gly |
| Pro | Ala 370 | Val | Thr | Gln | Tyr | Glu 375 | Ile | Gln | Pro | Ala | Gln 380 | Gly | Val | Lys | Val |
| Ser 385 | Lys | Ile | Val | Asn | Leu 390 | His | Asn | Asp | Ile | Ala 395 | Leu | Ala | Leu | Ala | Ala 400 |
| Lys | Asp | Val | Arg | Ile 405 | Glu | Ala | Pro | Ile | Pro 410 | Gly | Arg | Ser | Ala | Val 415 | Gly |
| Ile | Glu | Val | Pro 420 | Asn | Glu | Lys | Ile | Ser 425 | Leu | Val | Ser | Leu | Lys 430 | Glu | Val |
| Leu | Asp | Glu 435 | Lys | Phe | Pro | Ser | Asn 440 | Asn | Lys | Leu | Glu | Val 445 | Gly | Leu | Gly |
| Arg 450 | Asp | Ile | Ser | Gly | Asp 455 | Pro | Ile | Thr | Val | Pro 460 | Leu | Asn | Glu | Met | Pro |
| His 465 | Leu | Leu | Val | Ala | Gly 470 | Ser | Thr | Gly | Ser | Gly 475 | Lys | Ser | Val | Cys | Ile 480 |
| Asn | Gly | Ile | Ile | Thr 485 | Ser | Ile | Leu | Leu | Asn 490 | Ala | Lys | Pro | His | Glu 495 | Val |
| Lys | Leu | Met | Leu 500 | Ile | Asp | Pro | Lys | Met 505 | Val | Glu | Leu | Asn | Val 510 | Tyr | Asn |
| Gly | Ile | Pro | His | Leu 515 | Leu | Ile | Pro | Val 520 | Val | Thr | Asn | Pro | His 525 | Lys | Ala |
| Ala | Gln 530 | Ala | Leu | Glu | Lys | Ile 535 | Val | Ala | Glu | Met | Glu 540 | Arg | Arg | Tyr | Asp |
| Leu 545 | Phe | Gln | His | Ser | Ser 550 | Thr | Arg | Asn | Ile | Lys 555 | Gly | Tyr | Asn | Glu | Leu 560 |
| Ile | Arg | Lys | Gln | Asn 565 | Gln | Glu | Leu | Asp | Glu 570 | Lys | Gln | Pro | Glu | Leu 575 | Pro |
| Tyr | Ile | Val | Val 580 | Ile | Val | Asp | Glu | Leu 585 | Ala | Asp | Leu | Met | Met 590 | Val | Ala |
| Gly | Lys | Glu 595 | Val | Glu | Asn | Ala | Ile 600 | Gln | Arg | Ile | Thr | Gln 605 | Met | Ala | Arg |
| Ala | Ala 610 | Gly | Ile | His | Leu | Ile 615 | Val | Ala | Thr | Gln | Arg 620 | Pro | Ser | Val | Asp |
| Val 625 | Ile | Thr | Gly | Ile | Ile 630 | Lys | Asn | Asn | Ile | Pro 635 | Ser | Arg | Ile | Ala | Phe 640 |
| Ala | Val | Ser | Ser | Gln 645 | Thr | Asp | Ser | Arg | Thr 650 | Ile | Ile | Gly | Thr | Gly 655 | Gly |
| Ala | Glu | Lys | Leu 660 | Leu | Gly | Lys | Gly | Asp 665 | Met | Leu | Tyr | Val | Gly 670 | Asn | Gly |
| Asp | Ser | Ser 675 | Gln | Thr | Arg | Ile | Gln 680 | Gly | Ala | Phe | Leu | Ser 685 | Asp | Gln | Glu |
| Val | Gln 690 | Asp | Val | Val | Asn | Tyr 695 | Val | Val | Glu | Gln | Gln 700 | Ala | Asn | Tyr |
| Val 705 | Lys | Glu | Met | Glu | Pro 710 | Asp | Ala | Pro | Val | Asp 715 | Lys | Ser | Glu | Met | Lys 720 |
| Ser | Glu | Asp | Ala | Leu 725 | Tyr | Asp | Glu | Ala | Tyr 730 | Leu | Phe | Val | Val | Glu 735 | Gln |

```
Gln  Lys  Ala  Ser  Thr  Ser  Leu  Leu  Gln  Arg  Gln  Phe  Arg  Ile  Gly  Tyr
               740                      745                     750

Asn  Arg  Ala  Ser  Arg  Leu  Met  Asp  Asp  Leu  Glu  Arg  Asn  Gln  Val  Ile
               755                      760                     765

Gly  Pro  Gln  Lys  Gly  Ser  Lys  Pro  Arg  Gln  Val  Leu  Ile  Asp  Leu  Asn
     770                      775                          780

Asn  Asp  Glu  Val
785
```

( 2 ) INFORMATION FOR SEQ ID NO:3:

( i ) SEQUENCE CHARACTERISTICS:
        ( A ) LENGTH: 2241 base pairs
        ( B ) TYPE: nucleic acid
        ( C ) STRANDEDNESS: double
        ( D ) TOPOLOGY: linear ( i i ) MOLECULE TYPE: Genomic DNA ( x i ) SEQUENCE DESCRIPTION: SEQ ID NO:3:

```
ATGGTGTTGG  GTGTTTTCCA  ATTAGGAATA  ATCGGTCGTC  TAATTGACAG  CTTCTTTAAT    60
TATTTATTTG  GGTACAGTAG  ATATTTAACA  TATATTTTAG  TACTCTTAGC  AACTGGTTTT   120
ATTACATACT  CTAAACGTAT  TCCTAAAACT  AGACGAACGG  CTGGTTCGAT  TGTATTGCAA   180
ATTGCATTGC  TATTTGTATC  ACAGTTAGTT  TTTCATTTTA  ATAGTGGTAT  CAAAGCTGAA   240
AGAGAACCTG  TACTTTCTTA  TGTATATCAG  TCATACCAAC  ACAGTCATTT  TCCAAATTTT   300
GGTGGCGGTG  TATTAGGTTT  TTATTTATTA  GAGTTAAGCG  TACCTTTAAT  TTCATTATTT   360
GGTGTATGTA  TTATTACTAT  TTTATTATTA  TGCTCAAGTG  TTATTTTATT  AACAAACCAT   420
CAACATCGTG  ATGTTGCAAA  AGTTGCACTG  GAAAATATAA  AGCTTGGTT   TGGTTCATTT   480
AATGAAAAAA  TGTCGGAAAG  AAACCAAGAA  AAACAATTGA  AGCGTGAAGA  AAAAGCGAGA   540
CTTAAAGAAG  AACAAAAGGC  ACGTCAAAAT  GAACAGCCAC  AAATAAAAGA  TGTGAGTGAT   600
TTTACGGAAG  TGCCTCAAGA  AAGAGATATT  CCAATTTATG  GGCATACTGA  AAATGAAAGT   660
AAAAGCCAGT  GTCAACCAAG  TCGAAAAAAA  CGAGTGTTTG  ATGCAGAGAA  TAGTTCGAAT   720
AACATCGTAA  ATCATCAAGC  AGATCAGCAA  GAGCAATTAA  CAGAACAAAC  TCATAACAGT   780
GTTGAAAGTG  AAAACACTAT  TGAAGAAGCT  GGTGAAGTTA  CGAATGTATC  GTATGTTGTT   840
CCACCGTTAA  CTTTACTTAA  TCAACCTGCA  AAACAAAAAG  CAACATCTAA  AGCTGAAGTA   900
CAACGTAAAG  GACAAGTACT  AGAGAATACA  TTAAAAGATT  TTGGGGTAAA  TGCAAAAGTG   960
ACACAAATTA  AAATTGGTCC  TGCAGTAACT  CAATATGAAA  TTCAACCAGC  TCAAGGGGTT  1020
AAAGTGAGTA  AAATTGTAAA  CTTGCATAAT  GATATTGCAT  TAGCTTTAGC  AGCAAAAGAT  1080
GTTAGAATCG  AAGCACCAAT  ACCTGGTCGC  TCTGCAGTAG  GTATTGAAGT  GCCAAATGAG  1140
AAAATTTCAT  TAGTTTCACT  AAAAGAAGTT  TTAGATGAAA  AATTCCCGTC  TAATAATAAA  1200
CTAGAAGTTG  GATTAGGAAG  AGATATATCA  GGTGATCCAA  TTACTGTTCC  ACTAAATGAA  1260
ATGCCACACT  TATTGGTGGC  AGGATCGACG  GGTAGTGGTA  AATCTGTTTG  TATAAATGGT  1320
ATTATTACAA  GTATTTTATT  AAATGCTAAG  CCGCATGAAG  TTAAACTTAT  GTTAATCGAT  1380
CCGAAAATGG  TTGAACTAAA  TGTTTATAAC  GGAATTCCAC  ATTTATTAAT  TCCGGTTGTT  1440
ACAAATCCTC  ATAAAGCTGC  TCAAGCTTTA  GAAAAAATTG  TAGCTGAGAT  GGAAAGACGT  1500
TATGATTTAT  TCCAACATTC  ATCAACTAGA  AATATTAAAG  GTTATAACGA  ATTAATCCGT  1560
AAGCAAAATC  AAGAATTAGA  TGAGAAGCAA  CCAGAATTAC  CTTATATCGT  TGTTATTGTA  1620
```

-continued

```
GATGAGCTTG  CAGATTTAAT  GATGGTAGCT  GGTAAAGAAG  TTGAAAATGC  GATTCAACGT   1680

ATCACACAAA  TGGCACGTGC  AGCAGGTATA  CATTTGATTG  TAGCAACACA  AAGACCTTCT   1740

GTGGATGTAA  TTACAGGTAT  CATTAAAAAT  AACATTCCAT  CTAGAATTGC  TTTTGCTGTG   1800

AGTTCTCAAA  CAGATTCAAG  AACTATTATT  GGTACTGGCG  GCGCAGAAAA  GTTACTTGGT   1860

AAAGGTGACA  TGTTATACGT  TGGAAATGGT  GATTCATCAC  AAACACGTAT  TCAAGGGGCG   1920

TTTTTAAGTG  ACCAAGAGGT  GCAAGATGTT  GTAAATTATG  TAGTAGAACA  ACAACAGGCA   1980

AATTATGTAA  AAGAAATGGA  ACCAGATGCA  CCAGTGGATA  AATCGGAAAT  GAAAAGTGAA   2040

GATGCTTTAT  ATGATGAAGC  GTATTTGTTT  GTTGTTGAAC  AACAAAAGGC  AAGTACATCA   2100

TTGTTACAAC  GCCAATTTAG  AATTGGTTAT  AATAGAGCAT  CTAGGTTGAT  GGATGATTTA   2160

GAACGCAATC  AGGTAATCGG  TCCACAAAAA  GGAAGCAAGC  CTAGACAAGT  TTTAATAGAT   2220

CTTAATAATG  ACGAGGTGTA  A                                                2241
```

( 2 ) INFORMATION FOR SEQ ID NO:4:

( i ) SEQUENCE CHARACTERISTICS:
    ( A ) LENGTH: 746 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:4:

```
Met  Val  Leu  Gly  Val  Phe  Gln  Leu  Gly  Ile  Ile  Gly  Arg  Leu  Ile  Asp
 1              5                        10                       15
Ser  Phe  Phe  Asn  Tyr  Leu  Phe  Gly  Tyr  Ser  Arg  Tyr  Leu  Thr  Tyr  Ile
              20                       25                       30
Leu  Val  Leu  Leu  Ala  Thr  Gly  Phe  Ile  Thr  Tyr  Ser  Lys  Arg  Ile  Pro
         35                       40                       45
Lys  Thr  Arg  Arg  Thr  Ala  Gly  Ser  Ile  Val  Leu  Gln  Ile  Ala  Leu  Leu
     50                       55                       60
Phe  Val  Ser  Gln  Leu  Val  Phe  His  Phe  Asn  Ser  Gly  Ile  Lys  Ala  Glu
65                       70                       75                       80
Arg  Glu  Pro  Val  Leu  Ser  Tyr  Val  Tyr  Gln  Ser  Tyr  Gln  His  Ser  His
                    85                       90                       95
Phe  Pro  Asn  Phe  Gly  Gly  Gly  Val  Leu  Gly  Phe  Tyr  Leu  Leu  Glu  Leu
               100                      105                      110
Ser  Val  Pro  Leu  Ile  Ser  Leu  Phe  Gly  Val  Cys  Ile  Ile  Thr  Ile  Leu
          115                      120                      125
Leu  Leu  Cys  Ser  Ser  Val  Ile  Leu  Leu  Thr  Asn  His  Gln  His  Arg  Asp
     130                      135                      140
Val  Ala  Lys  Val  Ala  Leu  Glu  Asn  Ile  Lys  Ala  Trp  Phe  Gly  Ser  Phe
145                      150                      155                      160
Asn  Glu  Lys  Met  Ser  Glu  Arg  Asn  Gln  Glu  Lys  Gln  Leu  Lys  Arg  Glu
               165                      170                      175
Glu  Lys  Ala  Arg  Leu  Lys  Glu  Glu  Gln  Lys  Ala  Arg  Gln  Asn  Glu  Gln
          180                      185                      190
Pro  Gln  Ile  Lys  Asp  Val  Ser  Asp  Phe  Thr  Glu  Val  Pro  Gln  Glu  Arg
     195                      200                      205
Asp  Ile  Pro  Ile  Tyr  Gly  His  Thr  Glu  Asn  Glu  Ser  Lys  Ser  Gln  Cys
     210                      215                      220
Gln  Pro  Ser  Arg  Lys  Lys  Arg  Val  Phe  Asp  Ala  Glu  Asn  Ser  Ser  Asn
225                      230                      235                      240
```

```
Asn  Ile  Val  Asn  His  Gln  Ala  Asp  Gln  Gln  Glu  Gln  Leu  Thr  Glu  Gln
                    245            250                 255
Thr  His  Asn  Ser  Val  Glu  Ser  Glu  Asn  Thr  Ile  Glu  Glu  Ala  Gly  Glu
               260            265                      270
Val  Thr  Asn  Val  Ser  Tyr  Val  Pro  Pro  Leu  Thr  Leu  Asn  Gln
          275                 280                 285
Pro  Ala  Lys  Gln  Lys  Ala  Thr  Ser  Lys  Ala  Glu  Val  Gln  Arg  Lys  Gly
     290                      295                      300
Gln  Val  Leu  Glu  Asn  Thr  Leu  Lys  Asp  Phe  Gly  Val  Asn  Ala  Lys  Val
305                 310                 315                           320
Thr  Gln  Ile  Lys  Ile  Gly  Pro  Ala  Val  Thr  Gln  Tyr  Glu  Ile  Gln  Pro
                    325                 330                           335
Ala  Gln  Gly  Val  Lys  Val  Ser  Lys  Ile  Val  Asn  Leu  His  Asn  Asp  Ile
               340                 345                      350
Ala  Leu  Ala  Leu  Ala  Ala  Lys  Asp  Val  Arg  Ile  Glu  Ala  Pro  Ile  Pro
               355                 360                      365
Gly  Arg  Ser  Ala  Val  Gly  Ile  Glu  Val  Pro  Asn  Glu  Lys  Ile  Ser  Leu
     370                      375                 380
Val  Ser  Leu  Lys  Glu  Val  Leu  Asp  Glu  Lys  Phe  Pro  Ser  Asn  Asn  Lys
385                 390                 395                           400
Leu  Glu  Val  Gly  Leu  Gly  Arg  Asp  Ile  Ser  Gly  Asp  Pro  Ile  Thr  Val
                    405                 410                      415
Pro  Leu  Asn  Glu  Met  Pro  His  Leu  Leu  Val  Ala  Gly  Ser  Thr  Gly  Ser
               420                 425                      430
Gly  Lys  Ser  Val  Cys  Ile  Asn  Gly  Ile  Ile  Thr  Ser  Ile  Leu  Leu  Asn
          435                 440                      445
Ala  Lys  Pro  His  Glu  Val  Lys  Leu  Met  Leu  Ile  Asp  Pro  Lys  Met  Val
     450                 455                      460
Glu  Leu  Asn  Val  Tyr  Asn  Gly  Ile  Pro  His  Leu  Leu  Ile  Pro  Val  Val
465                 470                 475                           480
Thr  Asn  Pro  His  Lys  Ala  Ala  Gln  Ala  Leu  Glu  Lys  Ile  Val  Ala  Glu
               485                 490                      495
Met  Glu  Arg  Arg  Tyr  Asp  Leu  Phe  Gln  His  Ser  Ser  Thr  Arg  Asn  Ile
          500                 505                      510
Lys  Gly  Tyr  Asn  Glu  Leu  Ile  Arg  Lys  Gln  Asn  Gln  Glu  Leu  Asp  Glu
          515                 520                      525
Lys  Gln  Pro  Glu  Leu  Pro  Tyr  Ile  Val  Val  Ile  Val  Asp  Glu  Leu  Ala
     530                 535                      540
Asp  Leu  Met  Met  Val  Ala  Gly  Lys  Glu  Val  Glu  Asn  Ala  Ile  Gln  Arg
545                      550                 555                      560
Ile  Thr  Gln  Met  Ala  Arg  Ala  Ala  Gly  Ile  His  Leu  Ile  Val  Ala  Thr
                    565                 570                      575
Gln  Arg  Pro  Ser  Val  Asp  Val  Ile  Thr  Gly  Ile  Ile  Lys  Asn  Asn  Ile
               580                 585                      590
Pro  Ser  Arg  Ile  Ala  Phe  Ala  Val  Ser  Ser  Gln  Thr  Asp  Ser  Arg  Thr
     595                      600                 605
Ile  Ile  Gly  Thr  Gly  Gly  Ala  Glu  Lys  Leu  Leu  Gly  Lys  Gly  Asp  Met
     610                      615                 620
Leu  Tyr  Val  Gly  Asn  Gly  Asp  Ser  Ser  Gln  Thr  Arg  Ile  Gln  Gly  Ala
625                      630                 635                      640
Phe  Leu  Ser  Asp  Gln  Glu  Val  Gln  Asp  Val  Val  Asn  Tyr  Val  Val  Glu
                    645                 650                      655
Gln  Gln  Gln  Ala  Asn  Tyr  Val  Lys  Glu  Met  Glu  Pro  Asp  Ala  Pro  Val
               660                 665                      670
```

| | | | | | | | | | | | | | | |
|---|---|---|---|---|---|---|---|---|---|---|---|---|---|---|
| Asp | Lys | Ser 675 | Glu | Met | Lys | Ser | Glu 680 | Asp | Ala | Leu | Tyr | Asp 685 | Glu | Ala | Tyr |
| Leu | Phe 690 | Val | Val | Glu | Gln | Gln 695 | Lys | Ala | Ser | Thr | Ser 700 | Leu | Leu | Gln | Arg |
| Gln 705 | Phe | Arg | Ile | Gly | Tyr 710 | Asn | Arg | Ala | Ser | Arg 715 | Leu | Met | Asp | Asp | Leu 720 |
| Glu | Arg | Asn | Gln | Val 725 | Ile | Gly | Pro | Gln | Lys 730 | Gly | Ser | Lys | Pro | Arg 735 | Gln |
| Val | Leu | Ile | Asp 740 | Leu | Asn | Asn | Asp | Glu 745 | Val | | | | | | |